United States Patent [19]
Hornback et al.

[11] Patent Number: 5,734,057
[45] Date of Patent: Mar. 31, 1998

[54] HIV PROTEASE INHIBITORS AND INTERMEDIATES

[75] Inventors: William J. Hornback; John E. Munroe, both of Indianapolis, Ind.

[73] Assignee: Eli Lilly and Company, Indianapolis, Ind.

[21] Appl. No.: 695,150

[22] Filed: Aug. 5, 1996

Related U.S. Application Data

[62] Division of Ser. No. 190,809, Feb. 2, 1994, abandoned.

[51] Int. Cl.$^6$ .................. C07D 471/06; C07D 513/04
[52] U.S. Cl. ............................................... 546/114
[58] Field of Search ...................................... 546/114

[56] References Cited

U.S. PATENT DOCUMENTS

| | | | |
|---|---|---|---|
| 4,161,599 | 7/1979 | Maffrand | 546/114 |
| 4,174,448 | 11/1979 | Bousquet et al. | 546/114 |
| 4,749,692 | 6/1988 | Blanchard et al. | 514/301 |
| 5,026,700 | 6/1991 | Harrison et al. | 514/233.8 |
| 5,142,056 | 8/1992 | Kempe et al. | 546/265 |
| 5,196,438 | 3/1993 | Martin et al. | 514/311 |
| 5,232,928 | 8/1993 | Skiles | 514/291 |
| 5,480,887 | 1/1996 | Hornback | 514/301 |

FOREIGN PATENT DOCUMENTS

| | | |
|---|---|---|
| 0 337 714 | 10/1989 | European Pat. Off. . |
| 0 346 847 | 12/1989 | European Pat. Off. . |
| 0 361 341 | 4/1990 | European Pat. Off. . |
| 0 498 680 | 8/1992 | European Pat. Off. . |
| 0 539 192 | 4/1993 | European Pat. Off. . |
| WO 92/08701 | 5/1992 | WIPO . |
| WO 93/13066 | 7/1993 | WIPO . |

OTHER PUBLICATIONS

Roberts et al., Science, 248, 358–361 (1990).
Thaisrivongs et al., J. Med. Chem., 34, 2344–2356 (1991).
Ghosh et al., J. Med. Chem., 37, 1177–1188 (1994).
Ghosh et al., J. Med. Chem., 37, 2506–2508 (1994).
Kim et al., Tetrahedron Letters, 34(41), 6517–6520 (1993).
Kong–Teck Chong et al., J. Med. Chem., 36, 2575–2577 (1993).
Ghosh et al., J. Med. Chem., 36, 924–927 (1993), ibid 292–294.

*Primary Examiner*—C. Warren Ivy
*Assistant Examiner*—D. Margaret M. Mach
*Attorney, Agent, or Firm*—Janet T. McClain

[57] ABSTRACT

The present invention provides HIV protease inhibitors, intermediates for preparing HIV protease inhibitors. The enzyme, HIV protease, represents a viable target for the inhibition of HIV viral replication, thus providing a method for treating and/or preventing HIV infection.

9 Claims, 1 Drawing Sheet

FIGURE 1

HIV PROTEASE INHIBITORS AND INTERMEDIATES

This application is a division of application Ser. No. 08/190,809 filed Feb. 2, 1994 now abandoned.

BACKGROUND OF THE INVENTION

A retrovirus designated human immuno-deficiency virus (HIV) is the causative agent of the complex disease termed Acquired Immune Deficiency Syndrome (AIDS), and is a member of the lentivirus family of retroviruses. M. A. Gonda, F. Wong-Staal, R. C. Gallo, "Sequence Homology and Morphological Similarity of HTLV III And Visna Virus, A Pathogenic Lentivirus", Science, 227, 173, (1985); P. Sonigo, N. Alizon, et al., "Nucleotide Sequence of the Visna Lentivirus: Relationship to the AIDS Virus", Cell, 42, 369, (1985). The complex disease AIDS includes progressive destruction of the immune system and degeneration of the central and peripheral nervous systems. The HIV virus was previously known or referred to as LAV, HTLV-III or ARV.

A common feature of retrovirus replication is the post-translational processing of precursor polyproteins by a virally encoded protease to generate mature viral proteins required for viral assembly and function. interruption of this processing appears to prevent the production of normally infectious virus. Unprocessed structural proteins also have been observed in clones of non-infectious HIV strains isolated from human patients. The results suggest that the inhibition of HIV protease represents a viable method for the treatment or prevention of AIDS and/or the treatment or prevention of infection by HIV.

The HIV genome encodes structural protein precursors known as gag and pol, which are processed to afford the protease, reverse transcriptase and endonuclease/integrase. The protease further cleaves gag and gag-pol polyproteins to yield mature structural proteins of the virus core.

Considerable efforts are being directed toward the control of HIV by means of the structural protein precursors which are processed to yield the retroviral promease, reverse transcriptase and endonuclease/integrase. For example, a currently used therapeutic, AZT, is an inhibitor of the viral reverse transcriptase. H. Mitsuya, NS. Broder, "Inhibition of the In Vitro Infectivity in Cytopathic Effects of HTLV III", Proc. Natl. Acad. Sci. USA, 83, 1911 (1986).

Research efforts have also been directed toward HIV protease inhibitors. For example, European Patent Application (EPA) 361 341; EPA 346 847; EPA 402 646; and EPA 337 714 all disclose compounds which are said to be useful as HIV protease inhibitors.

Unfortunately, many of the known HIV protease inhibitors suffer from toxicity problems, lack of bioavailability or short in vivo half-lives. In particular, it is believed that oral bioavailability is a necessary characteristic of an HIV protease inhibitor due to the chronic nature of the disease. However, peptides and peptide mimetics are notorious for their inability to be orally absorbed. Thus, despite the recognized therapeutic potential associated with a protease inhibitor and the research efforts expended thus far, a viable therapeutic agent has not yet emerged.

The present invention provides compounds that inhibit HIV protease, thereby inhibiting the replication of HIV and providing a treatment and/or prevention of HIV infection.

The present invention provides intermediates that are useful for preparing a novel series of compounds that inhibit HIV protease. The compounds prepared using these intermediates possess desirable biological properties relative to previous HIV promease inhibitors while retaining potent HIV promease inhibitory activity. Thus, these HIV protease inhibitors promise to be useful for inhibiting HIV replication in an HIV infected cell, a cell susceptible to HIV infection or a primate in need thereof, thus treating and/or preventing HIV infection.

Other objects, features and advantages will become apparent to those skilled in the art from the following description and claims.

SUMMARY OF THE INVENTION

The present invention provides a compound of formula (I):

wherein:

$R^0$ and $R^1$ are independently hydrogen, $C_1$–$C_6$ alkyl, or hydroxy($C_1$–$C_6$)alkyl;

$R^2$ is hydrogen, an amino-protecting group, or a group of the formula:

$R^3$ is —$(CH_2)_i$-$R^{3a}$;

i is 0, 1, 2, 3, or 4;

$R^{3a}$ is aryl, —O-aryl, or —S-aryl;

$R^4$ is hydrogen or an amino-protecting group;

a, c and e are each independently 0, 1 or 2;

b and d are each independently 0 or 1;

$R^5$ is —$CH_2$—, —$CHR^{5x}$—, or —$CR^{5x}R^{5x}$—;

$R^6$ is —$CH_2$—, —$CHR^{6x}$—, or —$CR^{6x}R^{6x}$—;

$R^7$ is —$CH_2$—, —$CHR^{7x}$—, or —$CR^{7x}R^{7x}$—;

each of $R^{5x}$, $R^{6x}$, and $R^{7x}$ is independently selected from the group consisting of halo, hydroxy, $C_1$–$C_6$ alkyl, halo($C_1$–$C_6$)alkyl, hydroxy($C_1$–$C_6$)alkyl, $C_1$–$C_6$ alkoxy, $C_1$–$C_6$ alkylthio, $C_1$–$C_6$ alkylthio ($C_1$–$C_6$)alkyl, amino, or cyano;

X and Y are independently —S—, —S(O)—, —S(O)$_2$—, —O—, —NH—, or —N($R^9$)—; and $R^9$ is $C_1$–$C_6$ alkyl, aryl($C_1$–$C_6$)alkyl, aryl, or acyl;

with the provisos that:

b and d cannot both be 0;

the sum of a, b, c, d and e must be 2, 3, 4 or 5;

if $R^5$ is —$CR^{5x}R^{5x}$—, then $R^6$ must be —$CH_2$— or —$CHR^{6x}$—; and $R^7$ must be —$CH_2$— or —$CHR^{7x}$—;

if $R^6$ is —$CR^{6x}R^{6x}$—, then $R^5$ must be —$CH_2$— or —$CHR^{5x}$—; and $R^7$ must be —$CH_2$— or —$CHR^{7x}$—;

if $R^7$ is —$CR^{7x}R^{7x}$—, then $R^5$ must be —$CH_2$— or —$CHR^{5x}$—; and $R^6$ must be —$CH_2$— or —$CHR^{6x}$—;

or a pharmaceutically acceptable salt thereof.

DETAILED DESCRIPTION OF THE INVENTION

The present invention provides new compounds of formula (I), as described above, that are useful for preparing HIV protease inhibitors.

All temperatures stated herein are in degrees Celsius (°C.). All units of measurement employed herein are in weight units except for liquids which are in volume units.

The term "$C_1$–$C_6$ alkyl" represents a straight or branched alkyl chain having from one to six carbon atoms. Typical $C_1$–$C_6$ alkyl groups include methyl, ethyl, propyl, isopropyl, butyl, isobutyl, sec-butyl, t-butyl, pentyl, neo-pentyl, hexyl, and the like.

The term "halo" represents chloro, fluoro, bromo, or iodo.

The term "halo($C_1$–$C_6$)alkyl" represents a straight or branched alkyl chain having from one to six carbon atoms with 1, 2, or halo atoms attached to it. Typical halo($C_1$–$C_4$) alkyl groups include chloromethyl, trifluoromethyl, 2-chloroethyl, 3-bromopropyl, 2-fluoroisopropyl, 4-chlorobutyl, 2,3-dibromopentyl, and the like.

The term "hydroxy($C_1$–$C_6$)alkyl" represents a straight or branched alkyl chain having from one to six carbon atoms with a hydroxy group attached to it. Typical hydroxy($C_1$–$C_4$) alkyl groups include hydroxymethyl, 2-hydroxyethyl, 3-hydroxypropyl, 2-hydroxyisopropyl, 4-hydroxybutyl, 2-hydroxypentyl and the like.

The term "$C_1$–$C_6$ alkylthio" represents a straight or branched alkyl chain having from one to six carbon atoms attached to a sulfur atom. Typical $C_1$–$C_6$ alkylthio groups include methylthio, ethylthio, propylthio, isopropylthio, butylthio, sec-butylthio, t-butylthio, pentylthio, hexylthio, and the like.

The term "$C_1$–$C_6$ alkylthio($C_1$–$C_6$)alkyl" represents a straight or branched $C_1$–$C_6$ alkyl chain having from one to six carbon atoms with a $C_1$–$C_6$ alkylthio moiety attached to it. Typical $C_1$–$C_6$ alkylthio($C_1$–$C_6$)alkyl groups include methylthiomethyl, ethylthiomethyl, propylthioethyl, isopropylthiomethyl, butylthiopentyl, sec-butylthiomethyl, hexylthiopropyl, and the like.

The term "$C_1$–$C_6$ alkoxy" represents a straight or branched alkyl chain having from one to six carbon atoms attached to an oxygen atom. Typical $C_1$–$C_6$ alkoxy groups include methoxy, ethoxy, propoxy, isopropoxy, butoxy, sec-butoxy, t-butoxy, pentoxy, hexoxy, and the like. The term "$C_1$–$C_6$ alkoxy" includes within its definition the term "$C_1$–$C_4$ alkoxy".

"Aryl" represents a phenyl or naphthyl ring which is optionally substituted with halo, hydroxy, or $C_1$–$C_4$ alkoxy.

The term "aryl($C_1$–$C_6$)alkyl" represents a straight or branched alkyl chain having from one to six carbon atoms with an aryl group attached to it. Typical aryl($C_1$–$C_4$)alkyl groups include phenylmethyl, 2-naphth-1-ylethyl, 3-naphth-2-ylpropyl, 2-phenylisopropyl, 4-naphth-1-ylbutyl, 3-phenylpentyl, and the like.

The term "acyl" represents a $C_1$–$C_6$ alkyl or an aryl group attached to a carbonyl moiety. Typical acyl groups include formyl, acetyl, propanoyl, butanoyl, phenylcarbonyl, 2-methylphenylcarbonyl, 5-chloro-naphth-1-ylcarbonyl, naphth-2-ylcarbonyl, and the like.

The term "amino-protecting group" as used in the specification refers to substituents of the amino group commonly employed to block or protect the amino functionality while reacting other functional groups on the compound. Examples of such amino-protecting groups include formyl, trityl, benzyl, phthalimido, trichloroacetyl, chloroacetyl, bromoacetyl, iodoacetyl; or urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 2-(4-xenyl)isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl) prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)ethoxycarbonyl, 2-(methylsulfonyl)ethoxycarbonyl, 2-(triphenylphosphino) ethoxycarbonyl, fluorenylmethoxycarbonyl ("FMOC"), 2-(trimethylsilyl)ethoxycarbonyl, allyloxycarbonyl, 1-(trimethylsilylmethyl)prop-1-ethyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy) benzyloxycarbonyl, isobornyloxycarbonyl, 1-piperidyloxycarbonyl and the like; or benzoylmethylsulfonyl, 2-nitrophenylsulfenyl, diphenylphosphine oxide and like amino-protecting groups.

The species of amino-protecting group employed is not critical so long as the derivatized amino group is stable to the condition of subsequent reaction(s) on other positions of the intermediate molecule and can be selectively removed at the appropriate point without disrupting the remainder of the molecule including any other amino-protecting group(s). Preferred amino-protecting groups are t-butoxycarbonyl (t-Boc) and benzyloxycarbonyl (CbZ). Further examples of groups referred to by the above terms are described by J. W. Barton, "Protective Groups in Organic Chemistry", J. G. W. McOmie, Ed., Plenum Press, New York, N.Y., 1973, Chapter 2, and T. W. Greene, "Protective Groups in Organic Synthesis", John Wiley and sons, New York, N.Y., 1981, Chapter 7.

The compounds of the present invention have at least three asymmetric centers denoted by an asterisk in the formula below:

As a consequence of these asymmetric centers, the compounds of the present invention can occur as mixtures of diastereomers, racemic mixtures and as individual enantiomers. All asymmetric forms, individual isomers and combinations thereof, are within the scope of the present invention.

A preferred stereochemical configuration is (IA)

As mentioned above, the invention includes the pharmaceutically acceptable salts of the compounds defined by formula (I). A compound of this invention may possess a sufficiently acidic, a sufficiently basic, or both functional groups, and accordingly react with any of a number of inorganic bases, and inorganic and organic acids, to form a pharmaceutically acceptable salt.

The term "pharmaceutically acceptable salt" as used herein, refers to salts of the compounds of the above formula which are substantially non-toxic to living organisms. Typical pharmaceutically acceptable salts include those sales prepared by reaction of the compounds of the present invention with a mineral or organic acid or an inorganic base. Such salts are known as acid addition and base addition salts.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like.

Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, γ-hydroxybutyrate, glycollate, tartrate, methanesulfonate, propanesulfonate, naphthalene-1-sulfonate, napththalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate and the like. The potassium and sodium salt forms are particularly preferred.

It should be recognized that the particular counterion forming a part of any salt of this invention is not of a critical nature, so long as the salt as a whole is pharmacologically acceptable and as long as the counterion does not contribute undesired qualities to the salt as a whole.

Preferred compounds of this invention are those compounds of formula (IA):

or a pharmaceutically acceptable salt thereof.

Of these preferred compounds, more preferred are the compounds of formula (IA) where:

the sum of a, b, c, d, and e is 3 or 4;

$R^0$ and $R^1$ are independently hydrogen, or $C_1$–$C_6$ alkyl;

each of $R^{5x}$, $R^{6x}$, and $R^{7x}$ is independently selected from the group consisting of halo, or $C_1$–$C_6$ alkyl; and X and Y are independently —S—, —O—, or —NH—; or a pharmaceutically acceptable salt thereof.

Of these preferred compounds, especially preferred are those compounds where:

$R^2$ is hydrogen, t-butoxycarbonyl, benzyloxycarbonyl, or a group of the formula:

one of b and d is 0;

$R^3$ is —$CH_2$-$R^{3a}$;

$R^{3a}$ is aryl, or —S-aryl; and $R^4$ is hydrogen;

or a pharmaceutically acceptable salt thereof.

The most preferred compounds are:

N-t-butyl-octahydro-(3aR,7aS)-thieno[3,2-c]pyridine-(6S)-carboxamide;

N-t-butyl-octahydro-5[2R-hydroxy-4-phenyl-3S-N(benzyloxycarbonyl)amino-butyl]-(3aR,7aS)-thieno[3,2-c] pyridine-(6S)-carboxamide;

N-t-butyl-octahydro-5[2R-hydroxy-4-phenyl-3S-amino-butyl]-(3aR,7aS)-thieno[3,2-c] pyridine-(6S)-carboxamide;

N-t-butyl-octahydro-5[2R-hydroxy-4-thiophenyl-3R-N(benzyloxycarbonyl)amino-butyl]-(3aR,7aS)-thieno[3,2-c] pyridine-(6S)-carboxamide;

N-t-butyl-octahydro-5[2R-hydroxy-4-thiophenyl-3R-amino-butyl]-(3aR,7aS)-thieno[3,2-c] pyridine-(6S)-carboxamide;

or a pharmaceutically acceptable salt of any of the foregoing most preferred compounds.

Compounds of formula (IB)

where $R^0$, $R^1$, $R^3$, $R^4$, $R^5$, $R^6$, $R^7$, a, b, c, d, and e are as defined above in formula (I), may be used to prepare HIV protease inhibitors using a standard coupling reaction commonly employed in the synthesis of amides.

This coupling reaction is carried out by reacting an appropriately substituted amine of formula (IB), with an appropriately substituted carboxylic acid reactant of Z—COOH, where Z is defined below, in an aprotic solvent or mixture of solvents. The reaction is carried out in the presence or absence of a promoting agent, preferably in the presence of a promoting agent, and in the presence of a coupling reagent. Typical aprotic solvents for this reaction are tetrahydrofuran and dimethylformamide, or a mixture of such solvents. The reaction is carried out at a temperature from about −30° C. to about 25° C. The amine reactant is generally employed in equimolar proportions relative to the carboxylic acid reactant, in the presence of an equimolar quantity to a slight excess of the coupling reagent. Typical coupling reagents include the carbodiimides such as dicyclohexylcarbodiimide (DCC) and N,N'-diethylcarbodiimide; the imidazoles such as carbonyldiimidazole; as well as reagents such as bis(2-oxo-3-oxazolidinyl)phosphinic chloride (BOP-Cl) or N-ethoxycarbonyl-2-ethoxy-1,2-dihydroquinoline (EEDQ). A preferred coupling reagent for this reaction is DCC. A promoting agent is preferably included for this reaction; a preferred promoting agent is hydroxybenzotriazole hydrate (HOBT.H$_2$O).

Once the reaction is complete, the compound may be isolated, if desired, by procedures known in the for example, the compound may be crystallized and then collected by filtration, or the reaction solvent may be removed by extraction, evaporation or decantation. The compound may be further purified, if desired, by common techniques such as crystallization or chromatography over solid supports such as silica gel or alumina.

Compounds of formula (I) may be prepared according to the procedures shown in Reaction Scheme I.

where:

R$^4$, R$^3$, R$^0$, R$^1$, R$^5$, X, R$^6$, Y, R$^7$ a, b, c, d, and e are as defined above for formula (I);

R$^A$ is an amino-protecting group; and

Q on the bicyclic ring in reaction 1-3, above, represents the presence of double bonds between, for example, R$_a$ and R$_c$, R$_a$ and R$_d$, or R$_e$ and R$_c$ and the like, where b, b or d is 0, respectively.

Reaction Scheme I, above, is accomplished by carrying out reactions 1-3 (or 1-5) in sequential order. Once a reaction is complete, the intermediate compound may be isolated, if desired by procedures known in the art, for example, the compound may be crystallized and then collected by filtration, or the reaction solvent may be removed by extraction, evaporation or decantation. The intermediate compound may be further purified, if desired, by common techniques such as crystallization or chromatography over solid supports such as silica gel or alumina, before carrying out the next step of the reaction scheme.

Reaction I.1 is typically carried out by activating the carboxylic acid moiety using, for example, DCC, or a mixed anhydride such as isobutyl, followed by reaction with a primary or secondary amine having the formula NR$^0$R$^1$ where R$^0$ and R$^1$ are as defined above for formula (I). The reaction is typically carried out in a nonpolar aprotic solvent or mixture of solvents in the presence or absence of an acid scavenger at a temperature of from about −20° C. to about 25° C. to afford the corresponding amide. Suitable solvents for this reaction include ethers and chlorinated hydrocarbons, preferably diethyl ether, trichloroethane, or methylene chloride. Preferably, this reaction is preferably carried out in the presence of an acid scavenger such as a tertiary amine, preferably triethylamine. The amide afforded by this reaction may be isolated or further reacted as shown in Reaction 2.

Reaction I.2 is typically carried out by reacting the compound obtained from Reaction I.1 using the procedures detailed in *Comprehensive Organic Synthesis*, "Heteroatom Manipulation", Barry M. Trost, ed., volume 6, pages 736–746, (1991). In general, an appropriately substituted monocyclic ring is reacted with an aldehyde, such as formaldehyde or trichloroacetaldehyde in the presence of an acid. The acid may be used as a solvent. Typical acids include hydrochloric acid, hydrobromic acid, sulfuric acid, acetic acid, trifluoroacetic acid, and the like. A co-solvent may optionally be added to the reaction mixture. The co-solvent choice is not critical so long as the co-solvent employed is inert to the ongoing reaction and the reactants are sufficiently solubilized to effect the desired reaction. Typical solvents for this reaction include halogenated solvents such as methylene chloride, trichloroethane, carbontetrachloride, and the like. Alternatively, an aldehyde equivalent may be used, for example, dimethoxymethane and a suitable acid.

In reaction I.3, the compound isolated from reaction I.2 is reduced to provide a saturated heterocyclic compound as depicted above. Catalytic hydrogenation is a preferred method of reduction. Typical catalysts include palladium catalysts, rhodium catalysts (for example rhodium on alumina), rhenium catalysts and the like. Preferred catalysts include palladium-on-carbon. Suitable solvents for this reaction include the $C_1$–$C_4$ alcohols, tetrahydrofuran, acetic acid in alcohol, ethyl acetate and the like. A preferred solvent is ethanol. The reaction is typically carried out under an atmosphere of hydrogen from about 500 to about 4000 psi at a temperature of from about 25° C. to about 150° C. Preferably, the reaction is carried out under an atmosphere of hydrogen from about 2000 to about 3000 psi at a temperature of from about 50° C. to 100° C. The catalyst is generally employed in an amount ranging from about equivalent proportions to about a twelve-fold excess (by weight) of the reactant, preferably in about a six- to ten-fold excess (by weight) of the catalyst relative to the substrate.

Reactions I.4 and I.5 may be used to prepare compounds of formula (I) where $R^2$ is $R^3$ and $R^4$ are as defined above.

Reaction I.4 is a standard amino deprotection reaction using procedures and methods known in the art to afford the corresponding amine which is then used in Reaction I.5, above. Chemical deprotection procedures are preferred. For example, the compound isolated from I.3 may be deprotected using trimethylsilyliodide (TMSI) in an aprotic solvent or mixture of solvents at a temperature of from about 10° C. to 60° C., preferably at a temperature of from about 20° C. to 40° C. Typical solvents include methylene chloride, acetonitrile, trichloroethane, and the like.

In reaction I.5, the epoxide prepared in Reaction A.5, below, is reacted with compound isolated from Reaction I.4 in an alcoholic solvent at a temperature of from about 20° C. to 100° C. Solvent choice is not critical so long as the solvent employed is inert to the ongoing reaction and the reactants are sufficiently solubilized to effect the desired reaction. Typical solvents for this reaction include the alcohols, preferably isopropanol or ethanol. The reaction is preferably carried out at a temperature of about 65° C.

The compound isolated from reaction I.5 may optionally be deprotected to provide a compound of formula (IB) where $R^4$ is hydrogen.

The epoxide used in Reaction I.5 may be synthesized using Reaction Scheme A.

Reaction Scheme A

-continued
Reaction Scheme A where:
$R^4$ is an amino-protecting group;
$R^3$ is as defined above for formula (I); and
G is halo.

Reaction Scheme A, above, is accomplished by carrying out reactions 1–5 in sequential order. Once a reaction is complete, the intermediate compound may be isolated, if desired by procedures known in the art, for example, the compound may be crystallized and then collected by filtration, or the reaction solvent may be removed by extraction, evaporation or decantation. The intermediate compound may be further purified, if desired, by common techniques such as crystallization or chromatography over solid supports such as silica gel or alumina, before carrying out the next step of the reaction scheme.

Reaction A.1 is carried out by activating, that is, converting, an amino-protected carboxylic acid reactant having the structure:

to the corresponding mixed anhydride under conditions known in the art. For example, the amino-protected carboxylic acid reactant may be reacted with a $C_1$–$C_6$ alkylchloroformate, such as isobutylchloroformate preferably in the presence of an acid scavenger. Preferred acid scavengers are the trialkylamines, preferably triethylamine. The reaction is typically carried out in an aprotic solvent such as ethyl acetate. Solvent choice is not critical so long as the solvent employed is inert to the ongoing reaction and the reactants are sufficiently solubilized to effect the desired reaction. The resulting mixed anhydride reactant is preferably used in Reaction A.2 without further isolation or purification.

Reaction A.2 is accomplished in two steps. First, a solution of sodium hydroxide, covered with a layer of an ether solvent, preferably diethyl ether, is reacted with a large excess of N-methyl-N-nitro-N-nitrosoguanidine to form a diazomethane reactant. The sodium hydroxide is preferably used as an aqueous solution having about four to six mol/liter of sodium hydroxide. Once this reaction is substantially complete, the organic layer is dried over a dessicant such as potassium hydroxide. This solution is then reacted with the mixed anhydride from Reaction A.1, above, to form the corresponding α-diazo carbonyl compound. The diazomethane reactant is preferably used in this reaction without isolation or purification. The reaction is typically carried out at a temperature of from about −50° C. to about −10° C., preferably about −20° C.

In Reaction A.3, the α-diazo carbonyl compound prepared in Reaction A.2 is reacted with an acid of the formula H-G where G is halo, in an aprotic solvent such as diethylether to form an α-halo carbonyl compound. A preferred acid reactant is hydrochloric acid which provides the corresponding α-chloro carbonyl compound. The reaction is typically carried out at a temperature from about −30° C. to about 0° C. Solvent choice is not critical so long as the solvent employed is inert to the ongoing reaction and the reactants are sufficiently solubilized to effect the desired reaction. The acid reactant is typically added in the form of an anhydrous gas in small increments until the reaction appears substantially complete. The reaction can be monitored by thin layer chromatography.

In Reaction A.4, the carbonyl moiety on the compound prepared in Reaction A.3 is reduced using standard conditions known in the art to form the corresponding α-chloro hydroxy compound. For example, the compound prepared in Reaction A.3 is combined with a reducing agent in a mixture of solvents. Typical reducing agents include sodium borohydride, lithium borohydride, zinc borohydride, diisobutylaluminum hydride, and sodium bis(2-methoxyethoxy)aluminum hydride. A preferred reducing agent is sodium borohydride. Typical solvent mixtures include a protic and aprotic mixture such as tetrahydrofuran/water. Solvent choice is not critical so long as the solvent employed is inert to the ongoing reaction and the reactants are sufficiently solubilized to effect the desired reaction. The reaction is typically carried out at a temperature from about −10° C. to about 10° C., preferably about 0° C.

In Reaction A.5, the α-chloro hydroxy compound prepared in Reaction A.4 is treated with a strong base to form the corresponding epoxide (which is used above in Reaction I.5) under standard conditions known in the art. For example, the α-chloro hydroxy compound may be reacted with a potassium hydroxide/ethanol mixture in an alcoholic solvent such as ethanol. The reaction is typically carried out at a temperature from about 0° C. to about the reflux temperature of the solvent. Preferably the reaction is carried out at room temperature.

As noted above, the compound of the formula, Z—COOH represents a carboxylic acid reactant that may be coupled with the intermediates provided in the present application.

Typically, Z represents an appropriately substituted cyclic compound such as:

-continued where:
a is 1, 2, 3, 4, or 5;
b is 1, or 2;
c is 1, or 2;
d is 1, 2, 3, or 4;
each $R^2$ is independently hydrogen, hydroxy, thiol, halo, amino, $C_1$-$C_4$ alkylamino, di($C_1$-$C_4$)alkylamino, nitro, carboxy, $C_1$-$C_6$ alkyl, $C_1$-$C_6$ alkoxy, $C_1$-$C_6$ alkylthio, halo($C_1$-$C_4$)alkyl, hydroxy($C_1$-$C_4$)alkyl, $C_1$-$C_6$ alkylthio($C_1$-$C_6$)alkyl, $C_1$-$C_4$ alkoxycarbonyl, carbamoyl, N-($C_1$-$C_4$)alkylcarbamoyl, $C_1$-$C_4$ alkylsulfonyl, N,N-di($C_1$-$C_4$)alkylcarbamoyl, or $C_1$-$C_4$ alkylsulfonylamino;
$A^1$ and $A^2$ are independently —$CH_2$— or —N($R^8$)—;
$A^3$ and $A^4$ are independently —CH— or —N—;
$A^5$ and $A^6$ are independently —$CH_2$— or —N($R^9$)—;
$A^7$ and $A^8$ are independently —CH— or —N—;
$R^8$ is hydrogen or $C_1$-$C_4$ alkyl;
$R^9$ is hydrogen or $C_1$-$C_4$ alkyl;
or a pharmaceutically acceptable salt thereof.
Of these substituents,
Z is preferably where
$R^2$ is hydrogen, methyl, ethyl, propyl, chloro, fluoro, hydroxy, or amino; and
a is 2;
or a pharmaceutically acceptable salt thereof.

The carboxylic acid reactant, Z—COOH, used in Reaction I, to the extent not commercially available, can be prepared using known procedures. More particularly, this reactant may be prepared by further substitution and/or oxidation of a commercially available aryl or heterocyclic compound. For example, aryl or heterocyclic compounds of the formula Z—$CH_3$ may be oxidized using procedures known in the art. Specifically, the compound of the formula Z—$CH_3$ may be reacted with an oxidizing agent such as selenium dioxide or potassium permanganate at temperatures of from about 0° C. to 200° C. in a mutually inert solvent, such as water or diphenylether.

A second method for preparing compounds of the formula Z—COOH, involves protecting an appropriately substituted carboxylated aryl or heterocyclic with a carboxy-protecting group, and then further substituting the aryl or heterocyclic group using procedures known in the art. The carboxy-protecting group may then be removed using procedures known in the art to provide the desired carboxylic acid reactant, Z—COOH.

The term "carboxy-protecting group" as used in the specification refers to substituents of the carboxy group commonly employed to block or protect the carboxy functionality while reacting other functional groups on the compound. Examples of such carboxy-protecting groups include methyl, p-nitrobenzyl, p-methylbenzyl, p-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, t-butyl, t-amyl, trityl, 4-methoxytrityl, 4,4'-dimethoxytrityl, 4,4',4"-trimethoxytrityl, 2-phenylprop-2-yl, trimethylsilyl, t-butyldimethylsilyl, phenacyl, 2,2,2-trichloroethyl, β-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl and like moieties. A preferred method of protecting the carboxy group involves converting the carboxy moiety to an amide moiety and then hydrolyzing the amide back to provide the desired carboxy substituent. Further examples of these groups are found in E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5.

A preferred procedure for protecting the carboxy moiety involves the acid activation of the carboxy moiety, followed by the formation of an amide. For example, the carboxy moiety may be converted to an acyl halide, acyl anhydride, acyl imidazole and the like, preferably in the presence of an acid scavenger to form an activated carboxy moiety. A commercially available acid chloride is typically employed, obviating the need for further acid activation. Preferred acid scavengers are the trialkylamines, preferably methylamine. The reaction is typically carried out in an aprotic solvent such as diethyl ether, methylene chloride or the like. A preferred solvent is methylene chloride. Solvent choice is not critical so long as the solvent employed is inert to the ongoing reaction and the reactants are sufficiently solubilized to effect the desired reaction. The activated carboxy moiety is then reacted with an amine (R'—NH$_2$), for example aniline, in an aprotic solvent to provide an amide reactant, Z—C(O)NH—R' which may then be further substituted according to known procedures.

The amide reactant, Z—C(O)NH—R', may be further substituted by ortho deprotonation of the heterocyclic or aryl group, Z, to provide the corresponding anion followed by reaction with a variety of reagents such as alkyl halides, or halogenating agents such as bromine. The amide reactant is generally deprotonated twice using two equivalents of a strong base such as n-butyl lithium or sec-butyl lithium relative to the amide reactant, optionally in the presence of a metal coordinating agent such as tetramethylethylenediamine (TMEDA). The reaction is typically carried out in an aprotic solvent, preferably an ether such as diethyl ether, tetrahydrofuran or the like at a temperature from about −78° C. to about 25° C.

The resultant compound may then be hydrolyzed using procedures known in the art to provide the desired, substituted carboxylic acid reactant, Z—COOH. For example, a suitable hydrolysis involves exposing the amide reactant to a strong mineral acid, organic acid, or a mineral acid/organic mixture at a temperature from about 100° C. to about 160° C. Typical acids which may be used in this reaction include hydrobromic acid, acetic acid, hydrochloric acid and the like. A sealed tube may optionally be employed to accelerate the reaction rate.

A third method for preparing the substituted carboxylic acid reactant Z—COOH, involves diazotization of an aniline, followed by a quenching of the resultant diazonium salt. Specifically, the amino moiety of the aniline reactant is converted to a diazonium salt by reaction with nitrous acid. Nitrous acid may be produced in situ by treating sodium nitrite with an aqueous solution of a strong acid such as hydrochloric acid, or sulfuric acid. This reaction is typically carried out at or below 5° C. The diazonium salt is then quenched by reaction with suitable reagent to provide the desired substituted aromatic system. Representative quenching reagents include water, cyanide, halide, aqueous sulfuric acid, and the like. Typically, the reaction will be heated to facilitate the desired reaction.

There are a variety of reactions that are known in the art which may be used to produce the desired substitutions on the aryl or heterocyclic rings. For example, there are a variety of aromatic electrophilic and nucleophilic substitution reactions outlined in chapters 11 and 13 of March, J., "Advanced Organic Chemistry," 3rd edition, Wiley, 1985.

In addition, the compounds of the formula Z—COOH may be prepared by carboxylating an appropriately substituted aryl of heterocyclic compound. The carboxylation may be accomplished using a number of different reagents. For example, the aryl or heterocyclic reagent may be reacted with phosgene, oxalyl chloride, urea hydrochloride, or N,N-diethylcarbamoyl chloride in the presence of Friedel-Crafts catalysts. A variation of this method involves reacting the aryl or heterocyclic reagent with an alkyl thiolchloroformate (RSCOCl), or a carbamoyl chloride (H$_2$NCOCl) to provide an amide and a thiol ester, respectively. The amide and thiol ester may then be hydrolyzed to provide the desired carboxy group. March, at 491.

Examples of Friedel-Crafts catalysts include the Lewis acids, such as aluminum bromide (AlBr$_3$), aluminum chloride (AlCl$_3$), iron (III) chloride (FeCl$_3$), boron trichloride (BCl$_3$), boron trifluoride (BF$_3$), and the like. See also, March, J., "Advanced Organic Chemistry," $_3$rd edition, Wiley, 1985; Olah, "Friedel-Crafts and Related Reactions," Interscience, New York, 1963–1965; and Olah, "Friedel-Crafts Chemistry," Wiley, New York, 1973.

Additionally, the quinoline carboxylic acid reactants may be prepared by reacting an appropriately substituted aniline with glycerol using the Skraup reaction disclosed in Bradford, L. et al., J. Chem. Soc., 1947, p 437. For example, $_3$-amino benzoic acid may be reacted with glycerol in the presence of an oxidizing agent such as m-nitro benzene sulfonic acid or sodium m-nitro benzene sulfonate in a 60–75% aqueous solution of sulfuric acid to provide the desired carboxy-substituted quinoline. The reaction is typically carried out at a temperature from about $_{35}$° C. to reflux temperature for one to six hours, preferably from about 50° C. to reflux temperature for two to four hours.

The resultant reactants may then be reduced or hydrogenated using procedures known in the art. See e.g., March at 700. A preferred procedure involves catalytic hydrogenation, for example by combining the quinoline carboxylic acid reactant with hydrogen gas in the presence of a catalyst. A preferred catalyst is palladium-on-carbon. Typical solvents suitable for use in this reaction include any organic solvent such as ethyl acetate. Solvent choice is not critical so long as the solvent employed is inert to the ongoing reaction. The reaction is generally substantially complete after about 1 to 24 hours when conducted at a temperature in the range of from about 25° C. to about 100° C.

As noted above, all asymmetric forms, individual isomers and combinations thereof are considered part of this invention. Such isomers may be prepared from their respective precursors by the procedures described above, by resolving the racemic mixtures, or by separating the diastereomers. The resolution can be carried out in the presence of a resolving agent, by chromatography or by repeated crystallization or by some combination of these techniques which are known in the art. Further details regarding resolutions can be found in Jacques et al., Enantiomers, Racemates, and Resolutions, John Wiley & Sons 1981.

The compounds employed as initial starting materials in the synthesis of the compounds of this invention are known and, to the extent not commercially available are readily synthesized by standard procedures commonly employed by those in the art.

The pharmaceutically acceptable salts of the invention are typically formed by reacting a compound of formula (I) with an equimolar or excess amount of acid or base. The reactants are generally combined in a mutual solvent such as diethyl ether or benzene, for acid addition salts, or water or alcohols for base addition salts. The salts normally precipitate out of solution within about one hour to about ten days and can be isolated by filtration or other conventional methods.

The following Preparations and Examples further illustrate specific aspects of the present invention. It is to be understood, however, that these examples are included for illustrative purposes only and are not intended to limit the scope of the invention in any respect and should not be so construed.

In the following Preparations and Examples, the terms melting point, nuclear magnetic resonance spectra, electron impact mass spectra, field desorption mass spectra, fast atom bombardment mass spectra, infrared spectra, ultraviolet spectra, elemental analysis, high performance liquid chromatography, and thin layer chromatography are abbreviated "m.p.", "NMR", "EIMS", "MS(FD)", "MS(FAB)", "IR", "UV", "Analysis", "HPLC", and "TLC", respectively. In addition, the absorption maxima listed for the IR spectra are only those of interest and not all of the maxima observed.

In conjunction with the NMR spectra, the following abbreviations are used: "s" is singlet, "d" is doublet, "dd" is doublet of doublets, "t" is triplet, "q" is quartet, "m" is multiplet, "dm" is a doublet of multiplets and "br.s", "br.d", "br.t", and "br.m" are broad singlet, doublet, triplet, and multiplet respectively. "J" indicates the coupling constant in Hertz (Hz). Unless otherwise noted, NMR data refers to the free base of the subject compound.

The NMR spectra were obtained on a Brüker Corp. 270 MHz instrument or on a General Electric QE-$300$ 300 MHz instrument. The chemical shifts are expressed in delta ($\delta$) values (parts per million downfield from tetramethylsilane). MS(FD) spectra were taken on a Varian-MAT 731 Spectrometer using carbon dendrite emitters. EIMS spectra were obtained on a CEC 21-110 instrument from Consolidated Electrodynamics Corporation. MS(FAB) spectra were obtained on a VG ZAB-$3$ Spectrometer. IR spectra were obtained on a Perkin-Elmer 281 instrument. UV spectra were obtained on a Cary 118 instrument. TLC was carried out on E. Merck silica gel plates. Melting points are uncorrected.

EXAMPLE 1

A. (Z)-2-Methyl-4-thienylidene-5(4H)-oxazolone

A mixture of 70.6 g (602 mmol) of N-acetyl-glycine, 100 g (892 mmol) of 2-thiophene-carboxaldehyde (Aldrich), 142.3 mL (154 g, 1.51 mol) of acetic anhydride, and $_{36.6}$ g (446 mmol) of sodium acetate was heated on a steam bath for approximately one hour. The resultant reaction mixture was cooled to room temperature and then placed in a refrigerator overnight to provide a solid. This solid was suspended in 250 mL of cold water and then filtered through a Büchner funnel and washed with cold water. The resultant solid was reduced to dryness under reduced pressure to provide 65 g of the desired compound (56%).

B. (Z)-2-Acetamido-$_3$-(2-thienyl)-propenoic acid

A solution of 65 g of the subtitled compound of Example 1A in 240 mL of water and 620 mL of acetone was heated to reflux for approximately four hours. The resulting reaction mixture was cooled and then concentrated under reduced pressure to provide a solid. This solid was redissolved in 100 mL of water and 250 mL of methanol (heated to reflux to dissolve most of the solid) and then filtered hot. The filtrate was cooled resulting in the formation of crystals which were collected by filtration through a Büchner funnel, washed with water and reduced to dryness under reduced pressure to provide 55 g of the titled compound. This compound was used without further purification.

C. (S)-2-Acetamido-$_3$-(2-thienyl)-propanoic acid

A preformed catalyst was formed by adding $_{3.92}$ g of (+)-2,3-O-isopropylidene-2,3-dihydroxy-1,4-bis (diphenylphosphine)butane to 1.76 g of chloro(1,5-cyclooctadiene)-rhodium I dimer in 800 mL of toluene, under argon. The resultant mixture was stirred under argon for approximately twenty minutes. Meanwhile, 152 g (720 mmol) of the subtitled compound of Example 1B in 2500 mL of ethanol was shaken under 20 psi of hydrogen gas in a hydrogenation vessel for approximately twenty minutes. The preformed catalyst was then added the hydrogenation vessel, under nitrogen. The resultant reaction mixture was allowed to react at 50° C., under twenty psi of hydrogen gas for approximately sixteen hours. The reaction mixture was concentrated under reduced pressure to provide a brown solid which was treated with 700 mL of water containing 100 g of potassium carbonate. The resultant mixture was filtered through celite, washed with water and the filtrate was combined with diethyl ether. The resultant layers were separated and the aqueous layer was acidified with 5N hydrochloric acid, layered with 1000 mL of methylene chloride. The organic layer was then dried over sodium sulfate, filtered and concentrated to provide a tan solid which was purified by recrystallization from 900 mL of hot ethyl acetate to provide 109 g of the desired subtitled compound (71%).

D. N-Benzyloxycarbonyl-$\beta$-thienyl-L-alanine

A solution of 9.03 g (42.4 mmol) of the subtitled compound from Example 1C in 100 mL of 5N hydrochloric acid was heated to reflux for 2 hours. The resultant reaction mixture was cooled to 0° C. and made basic by adding 100 mL of a solution of $_{3.6}$M potassium carbonate. To this mixture was then added 150 mL of dioxane followed by 6.0 mL (42.4 mmol) of carbobenzyloxychloride in dioxane. When the reaction is substantially complete, as indicated by TLC (42/7/7/9, EtOAc/CH$_3$CN/H$_2$O/AcOH), the reaction mixture was concentrated, then washed with 100 mL of diethyl ether. The resultant layers were separated and the aqueous layer was acidified to pH<2 with 5N hydrochloric acid and extracted with methylene chloride which was then dried with sodium sulfate, filtered and concentrated under reduced pressure to provide 10.85 g of the titled compound (84%).

$[\alpha]_D$ (CDCl$_3$)=37.2° (at 22° C). $^1$H NMR ($_{300}$ MHz, CDCl$_3$): $\delta$ 7.37 (m, 5 H); 7.18 (d, J=4 Hz, 1 H); 6.95 (m, 1

H); 6.83 (m, 1 H); 5.35 (d, J=8 Hz, 1 H); 5.15 (s, 2 H); 4.7 (m, 1 H); and $_{3.4}$ (m, 2 H).

EXAMPLE 2

N-(Benzyloxycarbonyl) β-thienyl-D,L-alanine

To a mixture of $_{3.0}$ g (16.9 mmol) of β-thienyl-D,L-alanine in 75 mL of water and 60 mL of dioxane, was added 5.6 g (40.6 mmol) of anhydrous potassium carbonate, followed by 2.85 mL (20 mmol) of carbobenzyloxychloride. The resulting mixture was stirred rapidly for approximately one hour. When the reaction was substantially complete, as indicated by thin layer chromatography (21/7/7/9, EtOAc/AcOH/CH$_3$CN/H$_2$O), the reaction mixture was concentrated. The resultant layers were separated and the aqueous layer was washed with 75 mL of diethyl ether and then layered with 150 mL of methylene chloride. The resultant mixture was acidified with rapid stirring to pH=2.0 using 5N hydrochloric acid. The layers were then separated, and the organic layer was dried with sodium sulfate (Na$_2$SO$_4$), filtered and concentrated to provide 5.05 g of desired compound (98%).

$^1$H NMR ($_{300}$ MHz, CDCl$_3$): δ 7.37 (m, 5 H); 7.18 (d, J=4 Hz, 1 H); 6.95 (m, 1 H); 6.83 (m, 1 H); 5.35 (d, J=8 Hz, 1 H); 5.15 (s, 2 H); 4.7 (m, 1 H); and $_{3.4}$ (m, 2 H).

EXAMPLE 3

A. N-Carbobenzyloxy-β-thienyl-L-alanine-t-butylamide

To a cold (0° C.) mixture of 8.06 g (26.4 mmol) of the subtitled compound of Example 1D in 120 mL of tetrahydrofuran, was added 4.23 mL of N-methylmorpholine followed by the slow addition of 4.04 mL of isobutylchloroformate, and, after approximately fifteen minutes, 3.74 mL of t-butylamine. The resulting reaction mixture was warmed to room temperature, reacted for approximately two hours and then concentrated under reduced pressure to provide a residue. This residue was redissolved in ethyl acetate, and washed sequentially with water, a 1N solution of hydrochloric acid, and a saturated sodium bicarbonate solution. The combined organic portions was dried with sodium sulfate, filtered and concentrated to an oil. This oil was recrystallized from 100 mL of hot hexane to provide an oil which solidified on standing and was then dried to provide 9.25 g of solid (97%).

$^1$H NMR (300 MHz, CDCl$_3$): δ 7.37 (s, 5 H); 7.2 (d, J=4 Hz, 1 H); 6.95 (dd, J=4 Hz, 8 Hz, 1 H); 6.87 (d, J=4 Hz, 1 H); 5.52 (m, 2 H); 5.12 (s, 2 H); 4.27 (m, 1 H); 3.27 (m, 2 H), and 1.23 (s, 9 H).

B. N-t-Butyl-5-benzyloxycarbonyl-(4,5,6,7)-tetrahydrothieno[3,2-c]pyridine-(6S)-carboxamide To a solution of 500 mg (1.39 mmol) of the subtitled compound of Example 3A in 12 mL of 1,1,2-trichloroethane, was added 2 mL if trifluoroacetic acid, followed by 2 mL of dimethoxymethane. The resultant reaction mixture was refluxed for approximately fifteen minutes. When the reaction was substantially complete, as indicated by TLC, the reaction mixture was poured into a mixture of 3.5 g of potassium carbonate in 30 mL of water and 40 mL of methylene chloride. The resultant layers were separated, and the organic layer was dried with sodium sulfate, filtered and concentrated under reduced pressure to provide an oil. This oil was purified using flash chromatography (SiO$_2$; eluent of 3% ethyl acetate in methylene chloride) to provide 357 mg of the desired compound (69%).

$^1$H NMR (300 MHz, d$_6$ DMSO): δ 7.35 (m, 7 H); 6.83 (m, 1 H); 5.15 (m, 2 H); 4.98 (m, 1 H); 4.35 (m, 2 H); 3.10 (m, 2 H); and 1.10 (s, 9 H). MS: m/e 372 (M$^+$)

C. N-t-Butyl-5-benzyloxycarbonyl-octahydro-(3aR, 7aS)-thieno[3,2 -c]pyridine-(6S)-carboxamide To a high pressure hydrogenation vessel was placed 10.5 g (28.2 mmol) of the subtitled compound of Example 3B and 105 g of 5% palladium-on-carbon in 1100 mL of tetrahydrofuran and 525 mL of ethanol. The resultant reaction mixture was placed under hydrogen (3000 psi) at 80° C. for twenty four hours. The reaction mixture was cooled, filtered to remove the catalyst and then the catalyst was washed with 20% methanol in chloroform. The resultant organic portions were combined and concentrated under reduced pressure to provide a crude oil. This oil was redissolved in methylene chloride and purified using flash chromatography (SiO$_2$; eluent of 2% methanol in methylene chloride [on a smaller scale, an eluent of 1:2 diethyl ether in hexane containing 2% methanol]). to provide the desired cis isomer (major) comes through contaminated with small amount of a minor isomer. This mixture was recrystallized from a mixture of 1.5 mL methanol/20 mL diethyl ether/120 mL hexane to provide crystals that were filtered, washed with cold hexane and dried under reduced pressure to provide 2.54 g of the cis isomer (24%).

$^1$H NMR (300 MHz, CDCl3): δ 7.37 (s, 5 H); 6.0 and 5.5 (br.s, 1 H); 5.18 (br.s, 2 H); 4.22 (m, 2 H); 3.40 (m, 1 H); 2.87 (m, 3 H); 2.48 (m, 1 H); 2.15 (m, 2 H); 1.70 (m, 3 H); and 1.15 (br.s, 9 H). MS: m/e 377 (M$^+$ +1).

TABLE 1

Atomic coordinates (× 10$^4$) and equivalent isotropic displacement coefficients (Å$^2$ × 10$^3$)

| | x | y | z | U(eq) |
|---|---|---|---|---|
| S(1) | 173(2) | 9450(1) | 2158(1) | 93(1) |
| C(2) | −1195(6) | 10543(5) | 2239(3) | 97(3) |
| C(3) | −2297(6) | 10222(5) | 1709(3) | 82(2) |
| C(4) | −1529(5) | 9858(4) | 1059(2) | 61(2) |
| C(5) | −274(5) | 9071(4) | 1271(2) | 55(2) |
| C(6) | −642(5) | 7758(3) | 1204(2) | 53(2) |
| C(7) | −868(4) | 7454(3) | 434(2) | 41(1) |
| N(8) | −1687(4) | 8395(3) | 111(2) | 46(1) |
| C(9) | −2489(5) | 9189(4) | 558(2) | 58(2) |
| C(10) | −1948(5) | 8387(4) | −568(2) | 52(2) |
| O(11) | −2754(3) | 9044(3) | −873(2) | 68(1) |
| O(12) | −1161(3) | 7543(3) | −883(1) | 65(1) |
| C(13) | −1510(5) | 7230(5) | −1590(2) | 73(2) |
| C(14) | −298(4) | 7470(4) | −2055(2) | 50(1) |
| C(15) | −112(7) | 6744(5) | −2616(3) | 83(2) |
| C(16) | 998(8) | 6938(7) | −3073(3) | 110(3) |
| C(17) | 1897(7) | 7870(7) | −2955(3) | 101(3) |
| C(18) | 1719(7) | 8568(5) | −2387(3) | 91(3) |
| C(19) | 638(6) | 8361(5) | −1949(3) | 75(2) |
| C(20) | −1590(5) | 6252(4) | 360(2) | 47(2) |
| O(21) | −2847(3) | 6169(3) | 183(2) | 64(1) |
| N(22) | −771(4) | 5323(3) | 523(2) | 51(1) |
| C(23) | −1162(5) | 4052(4) | 477(3) | 58(2) |
| C(24) | 94(7) | 3365(4) | 730(3) | 101(3) |
| C(25) | −1484(8) | 3728(5) | −268(3) | 106(3) |
| C(26) | −2421(6) | 3775(5) | 924(3) | 96(3) |

*Equivalent isotropic U defined as one third of the trace of the orthogonalized U$_{ij}$ tensor

D. N-t-Butyl-octahydro-(3aR,7aS)-thieno[3,2-c]pyridine-(6S)-carboxamide

To a mixture of 2.41 g (6.4 mmol) of the subtitled compound of Example 3C in 12 mL of a 1:1 acetonitrile/methylene chloride solution, was added 1.9 mL of trimethylsilyliodide. After approximately ten minutes, an additional 0.94 mL of trimethylsilyliodide was added, followed by another 0.48 mL after ten minutes. The resultant mixture was reacted for approximately thirty minutes. When the reaction was substantially complete, as indicated by TLC, (5% ethyl acetate in methylene chloride), the reaction mixture was diluted with 30 mL of diethyl ether, 40 mL of water and 6 mL of a 1N hydrochloric acid solution. The resultant layers were separated and the organic layer was washed with 15 mL of a 0.1N hydrochloric acid solution. The combined aqueous portions were adjusted to pH 8 by the addition of a saturated sodium bicarbonate solution. The desired compound was extracted from the resultant solution using 200 mL of methylene chloride which was then dried with sodium sulfate, filtered and concentrated under reduced pressure to provide 1.3 g of the subtitled compound (84%).

$^1$H NMR (300 MHz, CDCl$_3$): δ 6.43 (s, 1 H); 3.22 (m, 2 H); 2.95 (m, 4 H); 2.17 (m, 3 H); 2.0 (m, 1 H); 1.55 (m, 2 H); and 1.32 (s, 9 H). [α]$_D$ (EtOH)=−179.1° (at 22° C.).

EXAMPLE 4

(±)-N-t-Butyl-octahydro-(3aR*,7aS*)-thieno[3,2-c]pyridine-(6S*)-carboxamide

The titled compound was prepared substantially in accordance with the procedure detailed in Example 3A–D, using the titled compound from Example 2.

EXAMPLE 5

N-t-Butyl-octahydro-5[2R-hydroxy-4-phenyl-3S-N(benzyloxycarbonyl)amino-butyl]-(3aR,7aS)-thieno[3,2-c]pyridine-(6S)-carboxamide A solution containing 145 mg (0.487 mmol) of 1S-[(1'S-N-(benzyloxycarbonyl)amino-2'-phenylethyl] oxirane and 118 mg (0.487 mmol) of the subtitled compound from Example 4 in 3 mL of ethanol was heated to 65° C. and reacted for approximately twenty hours. The resultant mixture was concentrated under reduced pressure to provide a crude material. This material was purified using radial chromatography (2000 micron plate; eluent of 1% methanol in chloroform) which separated the diastereomers to provide 98 mg of the titled compound (36%).

$^1$H NMR (300 MHz, CDCl$_3$): δ 7.25 (m, 10 H); 6.05 (m, 1 H); 5.13 (m, 1 H); 5.02 (s, 2 H); 3.97 (m, 1 H); 3.80 (m, 1 H); 3.37 (m, 1 H); 3.22 (m, 2 H); 2.95 (m, 4 H); 2.70 (m, 2 H); 2.58 (m, 1 H); 2.43 (m, 1 H); 2.32 (m, 1 H); 2.10 (m, 3 H); 1.90 (m, 1 H); and 1.30 (s, 9 H). MS: m/e 540 (M$^+$). In addition, 109 mg of another diastereomer was isolated from the reaction mixture (41%).

EXAMPLE 6

N-t-Butyl-octahydro-5[2R-hydroxy-4-phenyl-3S-amino-butyl]-(3aR,7aS)-thieno[3,2-c]pyridine-(6S)-carboxamide The desired subtitled compound was prepared substantially in accordance with the procedure detailed in Example 3D, using 85 mg (0.158 mmol) of the titled compound of Example 5, 101 μL (71 mmol) of trimethylsilyliodide in a 1:1 acetonitrile/methylene chloride mixture to provide 64 mg of a white solid (quantitative).

$^1$H NMR (300 MHz, CDCl$_3$): δ 7.28 (m, 5 H); 6.38 (s, 1 H); 3.75 (m, 1H); 3.32 (m, 2 H); 3.12 (m, 1 H); 2.93 (m, 2 H); 2.78 (m, 2 H); 2.58 (m, 3 H); 2.38 (m, 1 H); 2.12 (m, 5 H); 1.83 (m, 2 H); and 1.35 (s, 9 H).

EXAMPLE 7

N-t-Butyl-octahydro-5[2R-hydroxy-4-thiophenyl-3R-N(benzyloxycarbonyl)amino-butyl]-(3aR,7aS)-thieno[3,2-c] pyridine-(6S)-carboxamide A solution containing 1.45 g (4.4 mmol) of 1S-[(1'R-N-(benzyloxycarbonyl)amino-2'-(phenylthio)ethyl] oxirane and 1.07 g (4.4 mmol) of the subtitled compound from Example 3D in 30 mL of ethanol was heated to 65° C. and reacted for approximately sixty hours. The resultant mixture was concentrated under reduced pressure to provide a foam. This foam was purified using radial chromatography (4000 micron plate; eluent of 1% methanol in methylene chloride) to provide 1.8 g of the desired titled compound. Mixed fractions were combined to provide 326 mg of mixed diastereomers which were again purified using radial chromatography (2000 micron plate; eluent of 1% methanol in methylene chloride to provide an additional 228 mg of the desired compound.

Total yield: 2.03 g (80.5%). $^1$H NMR (300 MHz, CDCl$_3$): δ 7.30 (m, 10 H); 5.80 (m, 2 H); 5.08 (AB, 2 H); 3.95 (m, 2 H); 3.42 (m, 2 H); 3.17 (m, 3 H); 2.90 (m, 2 H); 2.67 (m, 1 H); 2.58 (m, 1 H); 2.48 (m, 1 H); 2.35 (m, 2 H); 1.98 (m, 4 H); and 1.30 (s, 9 H).

EXAMPLE 8

N-t-Butyl-octahydro-5[2R-hydroxy-4-thiophenyl-3R-amino-butyl]-(3aR,7aS)-thieno[3,2-c] pyridine-(6S)-carboxamide The desired titled compound was prepared substantially in accordance with the procedure detailed in Example 3D, using 1.8 g (3.15 mmol) of the subtitled compound of Example 7, 2.1 mL of trimethylsilyliodide in 20 mL of a 1:1 acetonitrile/methylene chloride mixture to provide 1.18 g of a white solid (86%).

$^1$H NMR (300 MHz, CDCl$_3$) δ 7.38 (m, 2 H); 7.28 (m, 2 H); 7.20 (m, 1 H); 6.23 (s, 2 H); 3.65 (s, 1 H); 3.28 (m, 3 H); 2.90 (m, 4 H); 2.70 (m, 2 H); 2.58 (m, 1 H); 2.43 (m, 1 H); 2.34 (m, 1 H); 2.05 (m, 4 H); 1.80 (m, 3 H); and 1.32 (s, 9 H). IR (CHCl3): 3430; 3005; 2973; 1670; 1514; 1456; 1366; and 1090 cm$^{-1}$. MS: m/e 437 (H$^+$).

As noted above, the compounds of the present invention are potent HIV protease inhibitors. They are also useful as intermediates for preparing HIV protease inhibitors with improved pharmacological properties.

For example, the following Examples 9 and 10 provide HIV protease inhibitors that have been synthesized and tested.

EXAMPLE 9

N-t-Butyl-octahydro-5[2R-hydroxy-3R-N(2'-methyl-3'-hydroxyphenylcarbonyl)amino-4-phenylthio-butyl]-(3aR,7aS)-thieno[3,2-c] pyridine-(6S)-carboxamide To a cold (−10° C.) solution containing 40 mg (0.914 mmol) of the titled compound from Example 8, 14 mg (0.093 mmol) of 2-methyl-3-carboxy-phenol and 12.6 mg (0.093 mmol) of hydroxybenzotriazole hydrate (HOBT.H$_2$O) in 2 mL of tetrahydrofuran, was added 18.7 mg (0.093 mmol) of dicyclohexylcarbodiimide (DCC). The reaction mixture was warmed to room temperature and allowed to react for approximately sixty hours. When the reaction was substantially complete, as indicated by TLC, the reaction mixture was diluted with 2 mL of diethyl ether and then filtered through a small cotton plug. The desired compound was isolated from the resultant filtrate using radial chromatography (2000 micron plate; eluent of 3% methanol in methylene chloride) to provide 44 mg of the titled compound (85%).

$^1$H NMR (300 MHz, CDCl$_3$): δ 7.42 (m, 2 H); 7.25 (m, 3 H); 7.07 (m, 3 H); 6.80 (d, J=8 Hz, 1 H); 5.80 (s, 1 H); 5.50 (s, 1 H); 4.42 (m, 1 H); 4.07 (m, 1 H); 3.88 (m, 1 H); 3.63 (m, 1 H); 3.45 (m, 1 H); 3.22 (m, 2 H); 2.92 (m, 2 H); 2.85 (s, 3 H); 2.64 (m, 1 H); 2.51 (m, 2 H); 2.38 (m, 1 H); 2.30 (s, 3 H); 2.08 (m, 2 H); 1.92 (m, 2 H); and 1.12 (s, 9 H).

EXAMPLE 10

N-t-Butyl-octahydro-5[2R-hydroxy-3R-N(2'-methyl-3'-hydroxyphenylcarbonyl)amino-4-phenylthiobutyl]-(3aR,7aS)-thieno[3,2-c] pyridine-(6S)-carboxamide methanesulfonate To a solution of 330 mg (0.577 mmol) of the titled compound of Example 9 in 6 mL of a 2:1 methylene chloride/acetonitrile mixture, was added 37.5 μL (0.577 mmol) of methanesulfonic acid, via syringe. When the reaction was substantially complete, the reaction mixture was concentrated under reduced pressure and then redissolved in methylene chloride, diethyl ether and hexane. The resultant mixture was concentrated under reduced pressure to provide a solid. This solid was suspended in hexane, sonicated and then concentrated to provide 385 mg of the desired titled compound (quantitative).

$^1$H NMR (300 MHz, CDCl$_3$): δ 7.42 (m, 2 H); 7.25 (m, 3 H); 7.07 (m, 3 H); 6.80 (d, J=8 Hz, 1 H); 5.80 (s, 1 H); 5.50 (s, 1 H); 4.42 (m, 1 H); 4.07 (m, 1 H); 3.88 (m, 1 H); 3.63 (m, 1 H); 3.45 (m, 1 H); 3.22 (m, 2 H); 2.92 (m, 2 H); 2.85 (s, 3 H); 2.64 (m, 1 H); 2.51 (m, 2 H); 2.38 (m, 1 H); 2.30 (s, 3 H); 2.08 (m, 2 H); 1.92 (m, 2 H); and 1.12 (s, 9 H).

As noted above, the compounds of formula (I) are useful as HIV protease inhibitors and for preparing HIV protease inhibitors. These compounds may be assayed using two assays: (1) an enzyme inhibition assay, and (2) an antiviral cell culture assay. These assays and the resultant data are provided below.

A Fluorescence HIV-1 Protease Inhibitor Assay was carried out to demonstrate the ability of the compounds of the present invention to inhibit HIV protease. This assay is described in detail in published European Patent Application (EPA) 0 526 009, herein incorporated by reference. Using this assay, a number of the compounds, prepared above, were assayed for HIV protease inhibitory activity.

The concentration of the tested compound that inhibits 50% of the enzyme (IC$_{50}$) is reported below in Table 1. The assay is unable to test compounds at less than a concentration of 0.16 ng/mL. Thus, some values are provided as % inhibition at [the stated] concentration (i.e. IC$_{74}$(0.16) represents the ability of the compound to inhibit 74% of the enzyme at 0.16 ng/mL).

TABLE 1

Inhibitory Activity of Formula (I) Compounds

| Example No. | Fluorescence Assay IC$_{50}$ in ng/mL |
|---|---|
| 5 | 3.4 |
| 7 | 1.9 |

TABLE 1-continued

Inhibitory Activity of Formula (I) Compounds

| Example No. | Fluorescence Assay IC$_{50}$ in ng/mL |
|---|---|
| 9 | 0.18 |
| 10 | IC$_{74}$(0.16) |

In addition, the compounds described in the present application may be tested using an antiviral cell culture assay as described in *Weislow, O. S.*, J. of National Cancer Institute, 81(8), pages 577–586 (Apr. 19, 1989) herein incorporated by reference.

This assay compares the viability of HIV-infected cells in a cell culture medium relative to the viability of such cells in the presence of a test compound. The concentration of test compound necessary to inhibit 90% of the virus is then measured using the viability of the cells as an indicator of viral inhibition. This assay is carried out using cell lines that are sensitive to the lyric effects of HIV infection.

Specifically, this assay utilizes the metabolic reduction of a tetrazolium reagent, 2,3-bis[2-methoxy-4-nitro-5-sulfophenyl]-5-[(phenylamino carbonyl]-2H-tetrazolium hydroxide (XTT). In the presence of a viable cell, the tetrazolium reagent, XTT, ms reduced to provide XTT formazan which may be quantified using colorimetric determination (at 450 nm). The intensity of the chromogenic signal is directly proportional to the concentration of the XTT formazan, thus providing a measure of the quantity of viable cells.

The compounds prepared in Examples 9 and 10, above, were tested using this assay. The concentration of the tested compound that inhibits 90% of the enzyme (IC$_{90}$) is reported below in Table 2.

TABLE 2

Antiviral Activity

| Example No. | IC$_{90}$ in nmol/L |
|---|---|
| 5 | 2000 |
| 9 | 17 |
| 10 | 10 |

Figure 1:
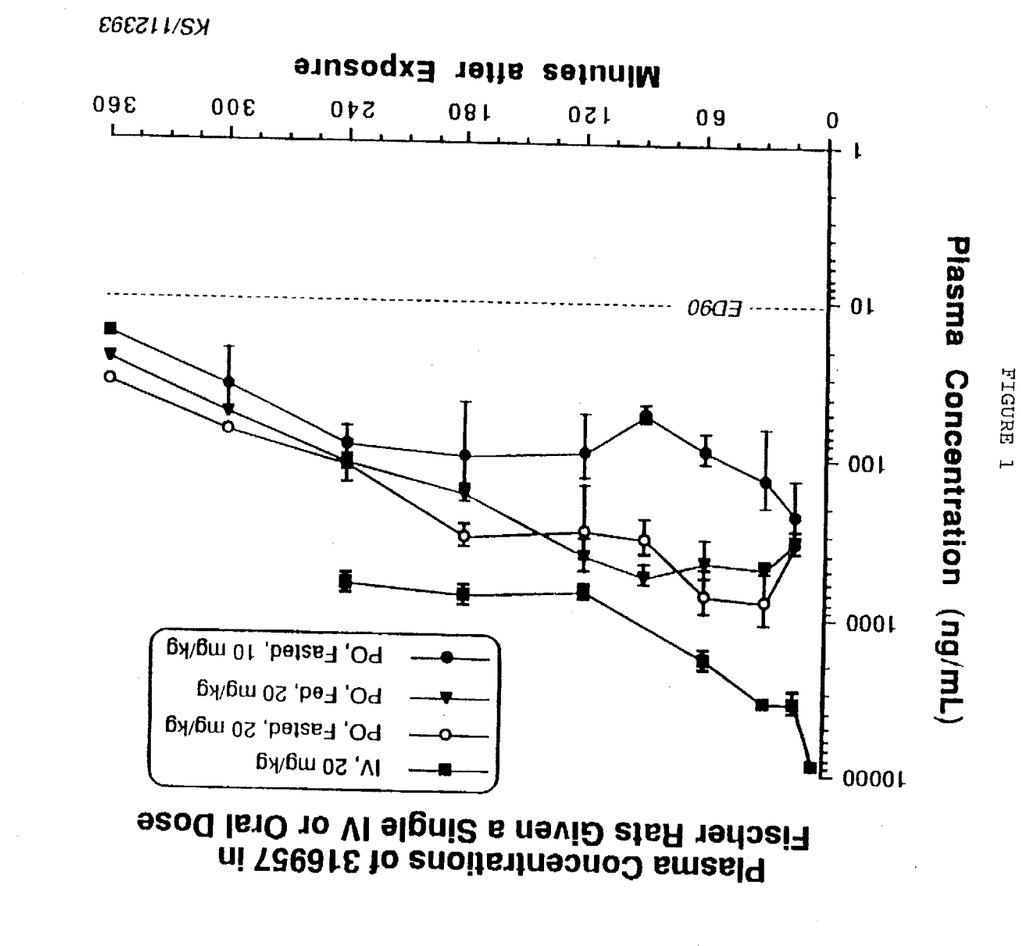

The compound prepared in Example 10 was also subjected to pharmacokinetic analysis using procedures that are standard in the art. Specifically, these properties were investigated following intravenous and oral administration in rats. For i.v. administration, the compound was injected from the tail vein whereas for oral administration, the compound was given by garage. Using a plot of concentrations versus time, the area under the curve (AUC) was calculated using the trapezoidal method. The oral bioavailability was calculated by comparing oral to intravenous AUC, with appropriate normalization for the size of each dose. The pharmacokinetic data for Example 10 is provided in FIG. 1.

We claim:

1. A compound of formula (I):

wherein:

R⁰ and R¹ are independently hydrogen, $C_1$–$C_6$ alkyl, or hydroxy($C_1$–$C_6$)alkyl;

R² is hydrogen, an amino-protecting group, or a group of the formula:

R³ is —(CH₂)ᵢ-R³ᵃ;
i is 0, 1, 2, 3, or 4;
R³ᵃ is aryl, —O-aryl, or —S-aryl;

R⁴ is hydrogen or an amino-protecting group;
a, c and e are each independently 0, 1 or 2;
b and d are each independently 0 or 1;
R⁵ is —CH₂—, —CHR⁵ˣ—, or —CR⁵ˣR⁵ˣ—;
R⁶ is —CH₂—, —CHR⁶ˣ—, or —CR⁶ˣR⁶ˣ—;
R⁷ is —CH₂—, —CHR⁷ˣ—, or —CR⁷ˣR⁷ˣ—;
  each of R⁵ˣ, R⁶ˣ, and R⁷ˣ is independently selected from the group consisting of halo, hydroxy, $C_1$–$C_6$ alkyl, halo($C_1$–$C_6$)alkyl, hydroxy($C_1$–$C_6$)alkyl, $C_1$–$C_6$ alkoxy, $C_1$–C6 alkylthio, $C_1$–$C_6$ alkylthio ($C_1$–$C_6$)alkyl, amino, or cyano; p1 X and Y are independently —S—, —S(O)— or —S(O)—;

with the provisos that:

one of b and d is 0;
b and d cannot both be 0;
the sum of a, b, c, d and e must be 3;
if R⁵ is —CR⁵ˣR⁵ˣ—, then R⁶ must be —CH₂— or —CHR⁶ˣ—; and R⁷ must be —CH₂— or —CHR⁷ˣ—;
if R⁶ is —CR⁶ˣR⁶ˣ—, then R⁵ must be —CH₂— or —CHR⁵ˣ—; and R⁷ must be —CH₂— or —CHR⁷ˣ—;
if R⁷ is —CR⁷ˣR⁷ˣ—, then R⁵ must be —CH₂— or —CHR⁵ˣ—; and R⁶ must be —CH₂— or —CHR⁶ˣ—;

or a pharmaceutically acceptable salt thereof.

2. A compound according to claim 1 of formula (IA):

or a pharmaceutically acceptable salt thereof.

3. A compound according to claim 2 wherein:

R⁰ and R¹ are independently hydrogen, or $C_1$–$C_6$ alkyl;
each of R⁵ˣ, R⁶ˣ, and R⁷ˣ is independently selected from the group consisting of halo, or $C_1$–$C_6$ alkyl;

or a pharmaceutically acceptable salt thereof.

4. A compound according to claim 3 wherein:

R² is hydrogen, t-butoxycarbonyl, benzyloxycarbonyl, or a group of the formula:

one of b and d is 0;
R³ is —CH₂-R³ᵃ;
R³ᵃ is aryl, or —S-aryl; and
R⁴ is hydrogen;

or a pharmaceutically acceptable salt thereof.

5. The compound according to claim 4 which is N-t-butyl-octahydro-(3aR,7aS)-thieno[3,2-c]pyridine-(6S)-carboxamide;

or a pharmaceutically acceptable salt thereof.

6. The compound according to claim 4 which is N-t-butyl-octahydro-5[2R-hydroxy-4-phenyl-3S-N(benzyloxycarbonyl)amino-butyl]-(3aR,7aS)-thieno[3,2-c] pyridine-(6S)-carboxamide;

or a pharmaceutically acceptable salt.

7. The compound according to claim 4 which is N-t-butyl-octahydro-5[2R-hydroxy-4-phenyl-3S-amino-butyl]-(3aR,7aS)-thieno[3,2-c] pyridine-(6S)-carboxamide;

or a pharmaceutically acceptable salt.

8. The compound according to claim 4 which is N-t-butyl-octahydro-5[2R-hydroxy-4-thiophenyl-3R-N(benzyloxycarbonyl)amino-butyl]-(3aR,7aS)-thieno[3,2-c] pyridine-(6S)-carboxamide;

or a pharmaceutically acceptable salt.

9. The compound according to claim 4 which is N-t-butyl-octahydro-5[2R-hydroxy-4-thiophenyl-3R-amino-butyl]-(3aR,7aS)-thieno[3,2-c] pyridine-(6S)-carboxamide;

or a pharmaceutically acceptable salt.

* * * * *